US012506255B2

(12) United States Patent
Te Velde et al.

(10) Patent No.: US 12,506,255 B2
(45) Date of Patent: Dec. 23, 2025

(54) WEARABLE DEVICE

(71) Applicant: smartQare B.V., Noordwijk (NL)

(72) Inventors: Mart Kornelis-Jan Te Velde, Helmond (NL); Mark Peter Paul Kleijnen, Eindhoven (NL); Timon Rutger Grob, Geldrop (NL)

(73) Assignee: smartQare B.V., Noordwijk (NL)

( * ) Notice: Subject to any disclaimer, the term of this patent is extended or adjusted under 35 U.S.C. 154(b) by 99 days.

(21) Appl. No.: 18/282,880

(22) PCT Filed: Mar. 30, 2022

(86) PCT No.: PCT/EP2022/058394

§ 371 (c)(1),
(2) Date: Sep. 19, 2023

(87) PCT Pub. No.: WO2022/214372

PCT Pub. Date: Oct. 13, 2022

(65) Prior Publication Data

US 2024/0170834 A1 May 23, 2024

(30) Foreign Application Priority Data

Apr. 6, 2021 (EP) .................................... 21166968

(51) Int. Cl.
*H01Q 1/27* (2006.01)
*A61B 5/00* (2006.01)
*H01Q 9/04* (2006.01)

(52) U.S. Cl.
CPC ........... *H01Q 1/273* (2013.01); *A61B 5/0022* (2013.01); *A61B 5/6833* (2013.01); *H01Q 9/0421* (2013.01)

(58) Field of Classification Search
CPC ....... A61B 5/0022; A61B 5/024; A61B 5/053; A61B 5/318; A61B 5/6833; H01Q 1/273; H01Q 9/0421
See application file for complete search history.

(56) References Cited

U.S. PATENT DOCUMENTS

| | | | | |
|---|---|---|---|---|
| 6,531,988 | B1 | 3/2003 | Koyama | |
| 10,129,635 | B1 * | 11/2018 | Zhu | H04R 1/1091 |
| 2008/0186241 | A1 | 8/2008 | Christensen | |
| 2009/0292193 | A1 * | 11/2009 | Wijesiriwardana | A61B 5/25 604/48 |
| 2010/0052897 | A1 * | 3/2010 | Allen | A61B 5/411 340/517 |

(Continued)

FOREIGN PATENT DOCUMENTS

| | | | | |
|---|---|---|---|---|
| EP | 3193705 | B1 | 4/2019 | |
| WO | WO 2019/183279 | A1 | 9/2019 | |

OTHER PUBLICATIONS

International Search Report Dated Jun. 28, 2022 for International Appln No. PCT/EP2022/058394 Filed Mar. 30, 2022.

(Continued)

*Primary Examiner* — Thien M Le
(74) *Attorney, Agent, or Firm* — Hoffmann & Baron, LLP

(57) ABSTRACT

A wearable device (10) has an internal antenna (22, 24) within a housing (20), and an external conductor patch (30) over which the housing (20) is mounted. The conductor patch (30) has an area greater than the area of an internal ground plane (22) of the antenna (22, 24).

13 Claims, 2 Drawing Sheets

(56) References Cited

U.S. PATENT DOCUMENTS

| | | | | |
|---|---|---|---|---|
| 2011/0166491 | A1* | 7/2011 | Sankai | A41D 13/1281<br>601/84 |
| 2012/0197150 | A1* | 8/2012 | Cao | A61B 5/6823<br>600/523 |
| 2014/0241131 | A1 | 8/2014 | Honda | |
| 2016/0004952 | A1 | 1/2016 | Mei | |
| 2017/0040681 | A1 | 2/2017 | Fujisawa | |
| 2018/0277957 | A1* | 9/2018 | Geist | H04B 5/26 |
| 2018/0294570 | A1* | 10/2018 | Stowell | H01Q 11/04 |
| 2018/0342794 | A1* | 11/2018 | Han | H04B 1/18 |
| 2019/0027822 | A1* | 1/2019 | Ayala Vazquez | H01Q 1/42 |
| 2019/0081615 | A1* | 3/2019 | Edwards | H03J 1/0083 |
| 2019/0223722 | A1 | 7/2019 | Xi | |
| 2019/0356042 | A1 | 11/2019 | Lo | |
| 2019/0379128 | A1 | 12/2019 | Tan | |
| 2022/0000376 | A1 | 1/2022 | Netil | |

OTHER PUBLICATIONS

Aobo Li, Shreya Singh and Dan Sievenpiper, “Metasurface and Their Applications”, Nanophotonics 2018; 7(6): 989-1011.

* cited by examiner

WEARABLE DEVICE

CROSS-REFERENCE TO PRIOR APPLICATIONS

This application is the U.S. National Phase application under 35 U.S.C. § 371 of International Application No. PCT/EP2022/058394, filed on Mar. 30, 2022, which claims the benefit of European Application No. 21166968.4 filed on Apr. 6, 2021. These applications are hereby incorporated by reference herein.

FIELD OF THE INVENTION

This invention relates to wearable devices, such as sensors, which report sensor data wirelessly.

BACKGROUND OF THE INVENTION

Wearable health patches with wireless sensor data communication are well known, for example for measuring biosignals such as heart rate and respiration rate and movement signals for example to detect activity levels, and posture (e.g. to detect a fall). Wearable devices are also well known which incorporate sensors for ambient conditions rather than biosignals, such as temperature and humidity.

Many different sensor types are therefore possible, such as for skin conductivity measurement, PPG measurement, motion measurement using accelerometers, temperature measurement, humidity measurement, and measurement of lighting levels etc.

Examples of suitable wireless communication systems are WiFi, Bluetooth, LoRa, 4G and 5G. However, any desired wireless communications modality may be integrated into a wearable device.

The wireless communication requires integration of an antenna into the wearable device. An antenna may for example be printed on a circuit board that carries the main sensor components and circuitry. The antenna may instead be a ceramic chip antenna which is mounted on the printed circuit board as a surface mount component or connected to the housing and connected to the antenna circuitry by spring clips or by a cable. The antenna is designed for miniaturization and accordingly will compromise on efficiency.

The range of a wireless signal from a wearable device is largely dependent on the execution of the antenna. The antenna design is especially important when a long range is needed in combination with low power consumption.

Miniaturized planar antennas as used in small wearable devices do not give optimal range and power consumption. Whip or stub antennas are more efficient, but they are not suited for wearable device such as wearable biosensors because of their size.

One particular issue resulting in the low efficiency mentioned above, and hence limited range and high power consumption, is the proximity of the antenna to the body against which the sensor is worn, for example where sensor signals are collected.

Thus, antennas that are currently used in health patches are a compromise between miniaturization and efficiency. They do not give an optimal range and power consumption. A particular problem is that in a miniaturized wearable device, the ground plane of the antenna is too small at low frequencies. This reduces efficiency and bandwidth.

US 2019/0356042 discloses a wearable device which incorporates an antenna structure having an antenna layer and a ground plane, and has an additional metal element between the antenna structure and the body of the user, to provide shielding. However, the antenna structure dimensions remain constrained by the size of the device, such as a watch.

There remains a need for an improved antenna configuration for use in a wireless wearable device.

SUMMARY OF THE INVENTION

The invention is defined by the independent claims. The dependent claims provide advantageous embodiments.

According to examples in accordance with an aspect of the invention, there is provided a wearable device comprising:

- a conductor patch;
- a housing;
- a wireless communications circuit mounted in the housing; and
- an antenna mounted in the housing and coupled to the wireless communications circuit, wherein the antenna comprises a ground plane, an antenna plane spaced from the ground plane, and a feed coupling between the ground plane and the antenna plane,
- wherein the housing is mounted over the conductor patch and the conductor patch has an area greater than the area of the ground plane.

The conductor patch may be used for application to the skin of a user.

This wearable device has an antenna internally within a housing, but there is additionally a conductor patch outside the housing. This conductor patch effectively extends the size of the internal ground plane of the antenna. In this way, the overall package of the sensor housing and the interface to the skin is used to optimize the antenna function.

The conductor patch has an area greater than the area of the coupling between the housing and the conductor patch. In other words, the conductor patch is larger than the housing (when viewed from above the skin on which the wearable device is mounted, i.e. in plan view). It thereby functions to extend the area of the ground plane.

The wearable device preferably further comprises an adhesive layer for attaching the conductor patch to the skin. The adhesive layer is used to fit the wearable device to the user.

The adhesive layer may be a conductive adhesive, which then provides electrical connection to the skin, or it may be a non-conductive adhesive, which instead interrupts the electrical connection to the skin. From the point of view of the antenna, either option is possible.

The wearable device may further comprise a ground interconnect between the conductor patch and the ground plane. The conductor patch may function as a screening/shielding layer if there is no direct (galvanic) electrical connection to the ground plane, whereas the use of a ground interconnect provides electrical connection to the conductor patch so that it effectively becomes part of the ground layer, but external to the housing.

The wearable device may further comprise a ground coupling between the ground plane and the antenna plane. This functions as a short pin, which is used in certain antenna designs, in addition to the feed coupling to the antenna plane.

The antenna may comprise a planar inverted F antenna. This type of antenna is well known for use in transmitting and receiving wireless mobile communications signals.

The antenna may comprise a stamped metal antenna comprising the antenna plane and connection legs for mounting the antenna plane on and over the ground plane.

The antenna may instead comprise a ceramic antenna with a metal coating.

The antenna may instead comprise a conductive layer provide on a surface of the housing. The conductive layer may for example be applied as a sticker or by using a laser direct structuring process.

Off-the-shelf antenna components may be used.

The wearable device may comprise a printed circuit board, which comprises a conductor area, which defines the ground plane, and a circuit area which carries the wireless communications circuit.

The wearable device is for example a wireless sensor device, and further comprises a sensor for collecting sensor data, wherein the wireless communications circuit is for wirelessly transmitting the sensor data using the antenna.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
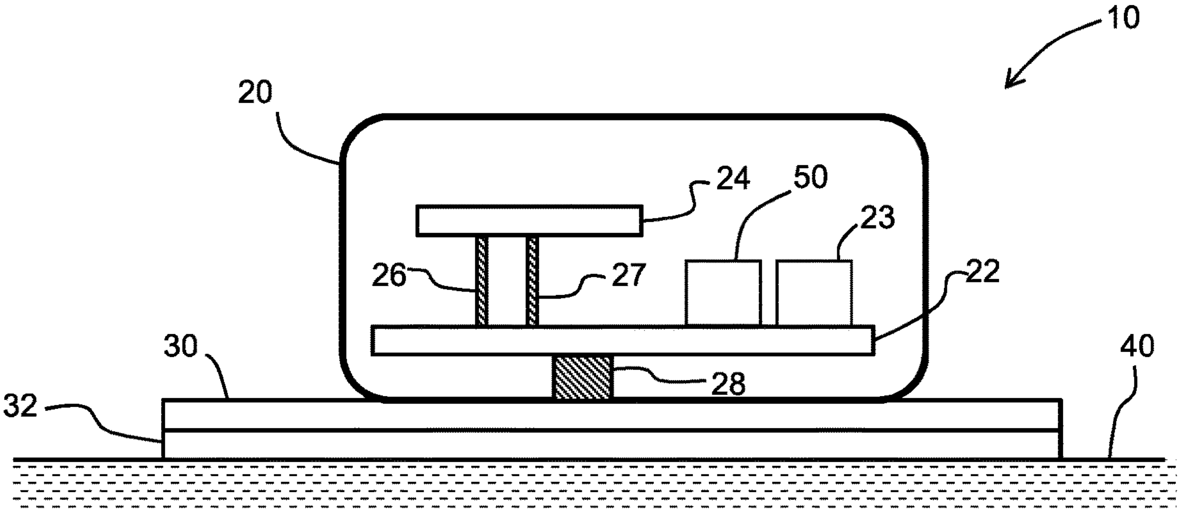
FIG. 1 shows an embodiment of a wearable device in side view.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a wearable device having an internal antenna within a housing, and an external conductor patch over which the housing is mounted. The conductor patch has an area greater than the area of an internal ground plane of the antenna and preferably greater than the area of the housing, which may be applied to the skin of the user. In an embodiment, the coupling of the wearable device to the skin, via the conductor patch, is used to improve the antenna performance, such as the operating bandwidth and power efficiency.

FIG. 1 shows a wearable device 10 in the form of a sensor comprising a housing 20, which is to be attached to the skin 40 of a subject. The housing is mounted on a conductor patch 30, and the combination of the housing 20 and the conductor patch 30 may be attached to the skin of the subject using an adhesive layer 32. An antenna is provided within the housing 20.

The adhesive layer 32 may be a conductive adhesive, for example if electrical contact to the skin is desired. However, a non-conductive adhesive may also be used. The material properties of the adhesive are not relevant to the antenna function. The adhesive layer 32 is a biocompatible material.

The conductor patch 30 may be formed from a variety of metals, such as silver, nickel, tin, copper, or combination of these metals. A conducting non-metal such as graphite may also be used. The thickness is for example between 10 μm and 200 μm.

Biocompatible materials may be used for the conductor patch 30, such as stainless steel 316L or biomedical grade graphite. For materials, which are not biocompatible, an additional shielding layer may be used to prevent direct skin contact, for example with shielding on both sides of the conductor patch 30.

The main purpose of the conductor patch 30 is to improve the antenna performance. However, the conductor patch 30 could also be used for sensing applications. For example, the sensing structure of a single-lead ECG sensor or bio-impedance sensor may be embedded within the conductor patch 30 or may be part of another conductive layer that makes electrical contact to the human body.

The conductor patch 30 may include an opening to enable access of a separate contact electrode (of a sensor) to the skin (e.g. for skin conductivity measurement) or to allow optical signals to pass through.

A small opening for this purpose will not have a significant adverse effect on the antenna performance. Preferably, the conductor patch 30 is a continuous layer, but even a split layer is possible with segments connected with a capacitor, such that RF currents can pass freely.

Within the housing 20, there is a wireless communications circuit 23, batteries 50 (or there may be an energy harvesting system) and the antenna.

The antenna is coupled to the wireless communications circuit 23, and comprises a ground plane 22 and an antenna plane 24 spaced from the ground plane. A feed coupling 26 is provided between the ground plane and the antenna plane. The dominant electric field is between the antenna plane and the ground plane.

The ground plane is formed as a conductor area of a printed circuit board.

The printed circuit board carries the wireless communications circuit as well as the batteries 50. The printed circuit board defines a feed pad for connection to the feed coupling 26, and conductor traces between the feed pad and the wireless communications circuit, thereby electrically connecting the antenna (in particular the antenna plane) to the wireless communications circuit 23.

The wireless communications circuit 23 (and other circuitry) may be under the antenna plane rather than laterally offset from the antenna place as is shown in FIG. 1. The antenna may for example cover the entire PCB.

High components such as a battery will negatively affect the antenna performance. There is also more generally an increased risk of self-pollution due to the noise of electrical components (e.g. a DC/DC converter) that will be picked up by the antenna. However, the benefit of a large antenna will outweigh these adverse effects.

The conductor patch 30 has an area greater than the area of the ground plane (i.e. the ground plane conductor area of the printed circuit board).

In the example shown, the conductor patch 30 is larger than the plan view area of the housing.

By way of example, the housing may have a maximum dimension (in plan view) of 5 cm. There is a specific category defined by cellular mobile network operators for small body worn devices. The antenna requirements for these types of device is more lenient than for other devices such as mobile phones. In order to fall into this category, the maximum dimension in any direction (e.g. the diagonal) is smaller than 5 cm.

By way of example the housing may have dimensions of approximately 4 cm×3 cm or 5 cm×2.5 cm, and hence an area in the range 10 cm 2 to 20 cm 2, such as 12 cm 2 to 15 cm 2.

The thickness of the housing is for example in the range 1 cm to 2 cm.

By way of example, the conductor patch may have dimensions (in plan view) of 6 cm×5 cm. More generally, the area of the conductor patch is for example in the range 20 cm 2 to 40 cm 2. The housing may be fully surrounded by the conductor patch (in plan view).

FIG. 1 additionally shows an optional ground coupling 27 between the ground plane 22 and the antenna plane 24. This functions as a short pin and its use depends on the type of antenna structure.

FIG. 1 additionally shows an optional ground interconnect 28 between the conductor patch 30 and the ground plane 22.

The conductor patch 30 may be isolated from the ground plane and function as a screening layer, or it may be electrically connected to the ground plane, and hence to the ground potential of the circuitry carried by the printed circuit board.

Electrical contact is made between the ground interconnect 28 and the conductor patch 30 as part of the manufacture of the device. The adhesive layer can also be applied 32 in the factory. The user then just needs to apply the already-applied adhesive to the skin, e.g. after removing a covering layer.

Alternatively, the conductor patch layer may be attached to the housing attached (e.g. soldered) in the factory, and the user then applies a separate adhesive to fix to the skin.

The increase in performance achieved by the invention is because the ground plane is extended by the conductor patch 30, in particular increasing the antenna efficiency and directing the antenna pattern away from the body. There is also a decreased sensitivity to the composition of the human body (such as the amount of fat and muscle). The conductor patch 30 will couple to the ground plane 22, through capacitive coupling, inductive coupling, or with the ground interconnect 28.

The physical properties of the materials close to the antenna determine the performance and design of the antenna. Optimizing an antenna on a body worn device is difficult because of the physical properties of the skin and body. The skin and body do not function as a good conductor or as a good insulator. There is also a spread in these properties, varying from person to person and the location on the body.

The conductor patch 30 provides a well-defined conductive surface between the antenna and the skin, and this leads to a better antenna performance, particularly for antenna designs with a spaced ground plane beneath the antenna plane. This applies regardless of whether or not there is electrical connection to the skin via the adhesive layer.

The antenna plane is in a different plane and further away from the body than the ground plane. Such antenna types can be planar inverted F (PIFA) antennas, patch antennas or monopole antennas.

A PIFA antenna for example includes the ground coupling 27, whereas other antenna types may not require this coupling. If the ground coupling 27 is not used, the antenna becomes a patch or monopole type antenna, depending on the shape.

The antenna plane 24 can be a simple metal plane, but the antenna resonance frequency is typically lowered to the desired frequency by adding a slot, in known manner.

It is noted that the invention relates particularly to antenna designs with a spaced ground plane and antenna plane. For systems where the antenna is in the same plane as the ground plane, the performance will be decreased by the presence of a conductive adhesive. This decrease in performance is caused because the conductive adhesive affects not only the ground plane, but also the antenna itself.

Figure 2:
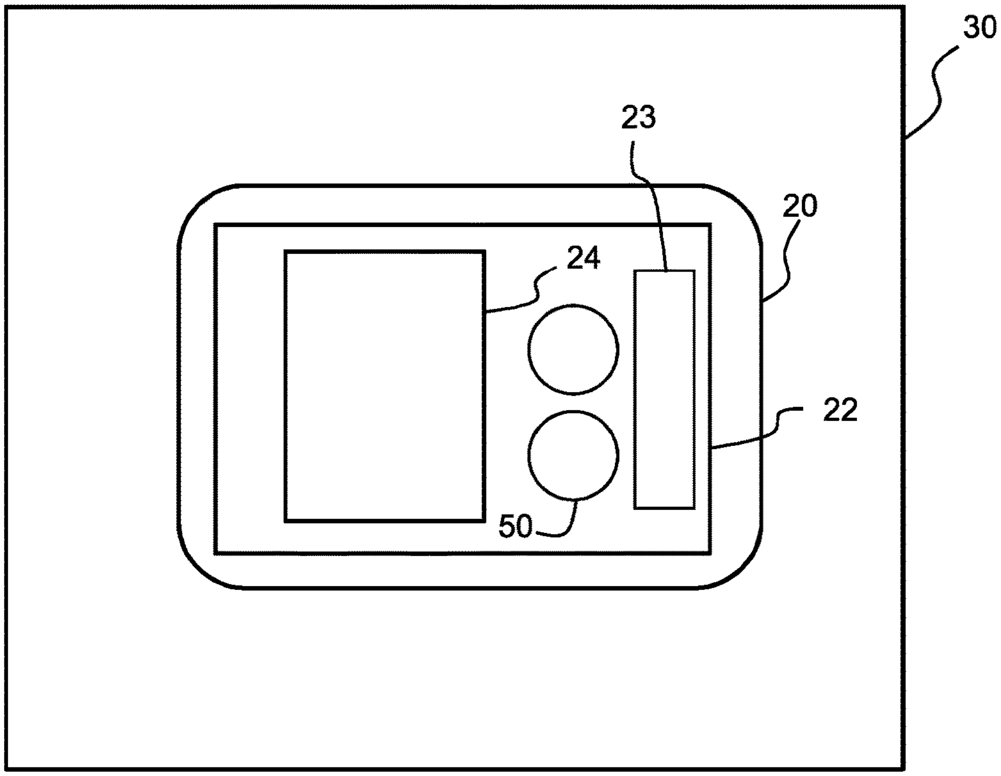
FIG. 2 shows the wearable device of FIG. 1 in plan view.

FIG. 2 shows the device of FIG. 1 in plan view.

Figure 3:
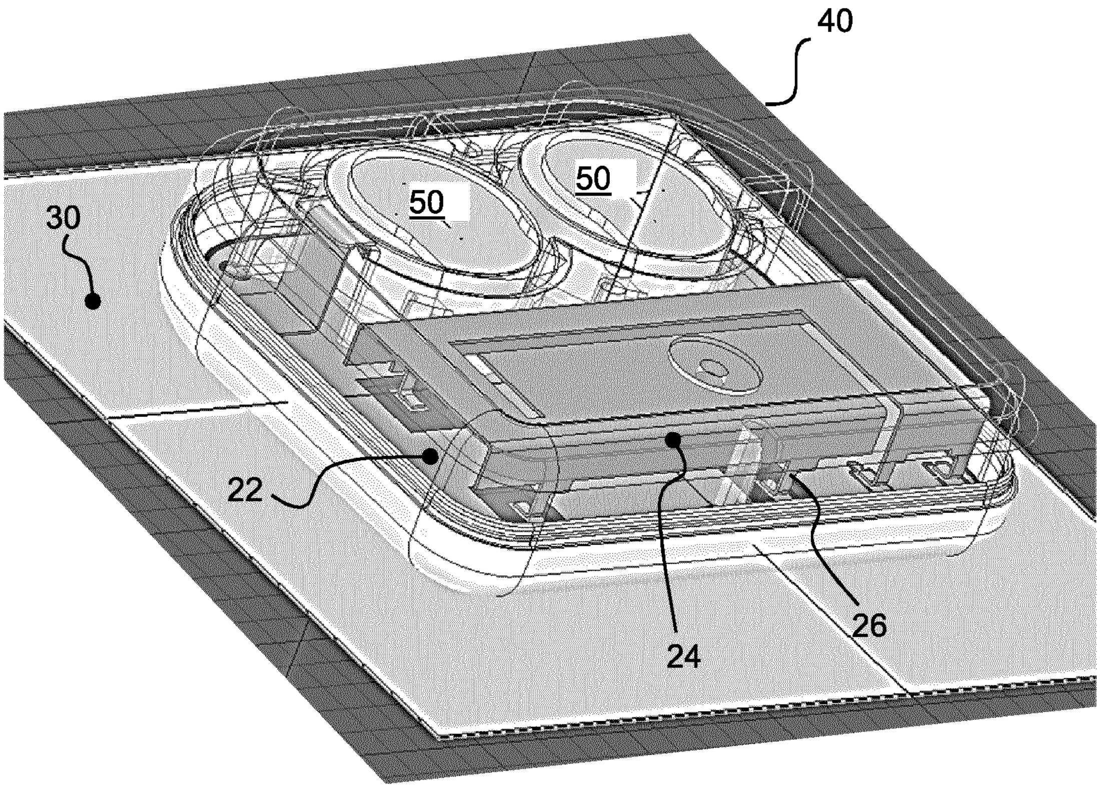
FIG. 3 shows a more detailed example of the wearable device of FIGS. 1 and 2 in perspective view, and transparent to show the internal components.

FIG. 3 shows a perspective 3D view of an example of a wearable device of the type shown schematically in FIGS. 1 and 2.

The antenna may comprise a stamped metal antenna comprising the antenna plane and connection legs for mounting the antenna plane above the ground plane. Thus, off-the-shelf antenna components may be used.

The wearable device may be a wireless sensor device, and further comprises a sensor for collecting sensor data (e.g. biosensor signals or ambient signals or movement signals), wherein the wireless communications circuit is for wirelessly transmitting the sensor data using the antenna.

Using simulations, the increase in overall radiation efficiency has found to be 1 dB without the use of the optional ground interconnect 28. The antenna also radiates less into the body, which is lost power due to the conductive properties of human tissue. Another benefit is that the Specific Absorption Rate (SAR) is decreased, so that the human exposure to electromagnetic radiation is reduced.

The use of the galvanic ground interconnect 28 between the conductor patch and the ground plane (and hence the electronics on the printed circuit board) has also been simulated and gave rise to a further increase of antenna efficiency to a total efficiency gain of 2.7 dB.

The example above makes use of a stamped metal antenna comprising the antenna plane and connection legs for mounting the antenna plane above the ground plane. However, other antenna designs may be used such as a ceramic antenna with a metal coating or a conductive layer provided on a surface of the housing.

The invention has been described with reference to a sensor patch. Such patches with wireless communication functionality are known for use as wearable biosensors and respiration sensors, for example for measuring heart rate, respiration rate, posture, activity levels and for fall detection.

However, the invention relates generally to a way to provide an antenna and associated wireless communication circuit in a compact way within a housing while maintaining antenna performance.

The data to be transmitted (or received) may not be sensor data—it may be any data generated or sensed at the device, which is to be transmitted. The antenna and communications circuit may instead be used to receive commands for controlling the device. Thus, the device may be an actuator rather than a sensor. It may of course have both sensing and actuation functionality and the wireless communication may be bidirectional, with a wireless transceiver circuit.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. Any reference signs in the claims should not be construed as limiting the scope. Measures recited in mutually different dependent claims can be advantageously combined.

The invention claimed is:

1. A wearable device comprising:

a conductor patch for application to a user's skin;

a housing, the conductor patch being outside the housing;

a wireless communications circuit mounted in the housing; and an antenna mounted in the housing and coupled to the wireless communications circuit, wherein the antenna comprises a ground plane, an antenna plane spaced from the ground plane, and a feed coupling between the ground plane and the antenna plane, wherein the housing is mounted over the conductor patch, and the conductor patch has an area greater than the area of the ground plane and greater than the area of the coupling between the housing and the conductor patch.

2. The wearable device of claim 1, wherein the housing has a maximum dimension in plan view of 5 cm.

3. The wearable device of claim 2, wherein the housing has an area in plan view in the range 10 $cm^2$ to 20 $cm^2$.

4. The wearable device of claim 3, wherein the area of the conductor patch is in the range 20 $cm^2$ to 40 $cm^2$.

5. The wearable device of claim 1, further comprising an adhesive layer for attaching the conductor patch to a user's skin.

6. The wearable device of claim 5, wherein the adhesive layer is a conductive adhesive.

7. The wearable device of claim 1, further comprising a ground interconnect between the conductor patch and the ground plane.

8. The wearable device of claim 1, further comprising a ground coupling between the ground plane and the antenna plane.

9. The wearable device of claim 1, wherein the antenna comprises a stamped metal antenna comprising the antenna plane and connection legs for mounting the antenna plane above the ground plane.

10. The wearable device of claim 1, wherein the antenna comprises a ceramic antenna with a metal coating.

11. The wearable device of claim 1, wherein the antenna comprises a conductive layer provided on a surface of the housing.

12. The wearable device of claim 1, comprising a printed circuit board which comprises a conductor area which defines the ground plane, and also defines a circuit area and which carries the wireless communications circuit.

13. The wearable device of claim 1, comprising a sensor for collecting sensor data, wherein the wireless communications circuit is for wirelessly transmitting the sensor data using the antenna.

* * * * *